United States Patent [19]

Shroot et al.

[11] Patent Number: 5,066,427
[45] Date of Patent: Nov. 19, 1991

[54] EICOSATRIYNOIC ACID ESTERS AND THEIR APPLICATION IN PHARMACEUTICAL AND COSMETIC PRACTICE

[75] Inventors: Braham Shroot, Antibes; Christopher Hensby, Biot; Jean Maignan, Tremblay les Gonesses; Gerard Lang, Saint Gratien; Serge Restle, Aulnay sous Bois; Michel Colin, Livry Gargan, all of France

[73] Assignee: Centre International de Recherches Dermatologiques dite CIRD, Valbonne, France

[21] Appl. No.: 411,043

[22] Filed: Sep. 22, 1989

Related U.S. Application Data

[62] Division of Ser. No. 881,776, Jul. 3, 1986, Pat. No. 4,877,789.

[30] Foreign Application Priority Data

Jul. 5, 1985 [FR] France ................................ 85 10363

[51] Int. Cl.$^5$ ................................................. C11C 1/00
[52] U.S. Cl. ............................................ 260/413; 574/886
[58] Field of Search ............... 260/413; 514/381, 255, 514/573, 558, 886

[56] References Cited

PUBLICATIONS

Chemical Abstracts, vol. 107, No. 22, 1987, 205184n.
Chemical Abstracts, vol. 86, No. 17, 1977, 120259p.
Chemical Abstracts, vol. 86, #17, 1976, 120200n.

*Primary Examiner*—Jose G. Dees
*Attorney, Agent, or Firm*—Cushman, Darby & Cushman

[57] ABSTRACT

Compound, corresponding to the formula

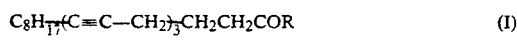

(I)

in which R is a $C_1$–$C_8$ lower alkoxy or $C_4$–$C_6$ cycloalkoxy group, substituted with one or more hydroxyl groups and/or interrupted by one or more hetero atoms chosen from oxygen and sulphur, an amino group of structure

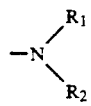

in which $R_1$ or $R_2$, which may be identical or different, denote a hydrogen atom or a linear or branched $C_1$–$C_8$ lower alkyl radical, optionally interrupted by one or more hetero atoms chosen from oxygen, sulphur and nitrogen, this alkyl radical being able to be substituted with one or more hydroxyl groups, $R_1$ and $R_2$ not being able to denote hydrogen simultaneously, or alternatively $R_1$ and $R_2$ form, together with the nitrogen atom, a heterocyclic system optionally containing oxygen, sulphur or nitrogen as an additional hetero atom, one of the radicals $R_1$ and $R_2$ also being able to denote, when the other is a hydrogen atom, an aryl radical of formula (II):

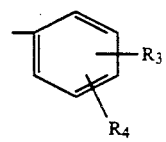

(II)

or alternatively a benzyl radical of formula (III):

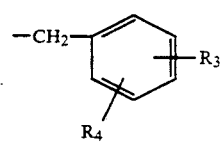

(III)

in which formulae $R_3$ and $R_4$, denote, independently of each other, a hydrogen atom, a $C_1$–$C_4$ alkyl radical, a hydroxyl group, a halogen atom or a carboxyl or trifluoromethyl group, the amine group also being able to originate from a sugar, and also the isomers and salts thereof which are pharmaceutically and cosmetically acceptable.

12 Claims, No Drawings

EICOSATRIYNOIC ACID ESTERS AND THEIR APPLICATION IN PHARMACEUTICAL AND COSMETIC PRACTICE

This is a division of application Ser. No. 881,776, filed July 3, 1986, now U.S. Pat. No. 4,877,789.

The subject of the present invention is new compounds consisting of eicosatriynoic acid esters and amides, and also their application, on the one hand as a therapeutic agent in the treatment or prophylaxis of allergic diseases and in the treatment of dermatoses and inflammatory diseases, and on the other hand in cosmetic compositions.

It is known that a number of substances perform an important role in the inflammatory process of the skin, such as acne, dermatoses such as, for example, psoriasis, eczema, and the like. These substances, including prostaglandins, hydroxyeicosatetraenoic acids, thromboxanes and leukotrienes, all have a common origin, namely arachidonic acid (see "VOORHEES, Leukotrienes and Other Lipoxygenase Products in the Pathogenesis and Therapy of Psoriasis and Other Dermatoses" Arch Dermatol. Vol. 119, July 1983, 541–547).

The formation of these substances results mainly from the release of arachidonic acid bound through an ester bond to the lipids present in the epidermis (for example the phospholipids).

For the treatment of skin diseases, prior recommendations have already been made to use either cyclooxygenase inhibitors, which inhibit prostaglandin formation, such as indomethacin, vitamin E, and the like, or substances capable of inhibiting lipoxygenases, such as eicosatetraynoic acid.

For the treatment of psoriasis, 5,8,11,14-eicosatetraynoic acid and also 5,8,11-eicosatriynoic acid, and their lower alkyl esters, have already been recommended (U.S. patent application Ser. No. 4,190,669).

The applicants have discovered that, surprisingly, particular esters or amides of 5,8,11-eicosatriynoic acid inhibited the enzymatic metabolism of arachidonic acid induced by cyclooxygenase and lipoxygenases. This result is especially unexpected in view of the blocking of the acidic function in the form of the esters or amides defined below.

These compounds show, moreover, a bioavailability which is different from that of the corresponding acids and which endows them with improved therapeutic properties.

The subject of the present invention is hence the new 5,8,11-eicosatriynoic acid derivatives.

Another subject of the invention consists of the pharmaceutical compositions containing such compounds as an active substance.

Another subject of the invention also consists of the process for preparing these derivatives.

The subject of the invention is also the use of these compounds in the cosmetics field, in particular in compositions for treating acne and compositions for use before or after exposure to sunlight, or in the treatment of seborrhoeic dermatitis.

Other subjects of the invention will emerge on reading the description and the examples which follow.

The compounds according to the invention are essentially characterized in that they correspond to the formula:

(I)

in which:

R is a $C_1$-$C_8$ lower alkoxy or $C_4$-$C_6$ cycloalkoxy group, substituted with one or more hydroxyl groups and/or interrupted by one or more hetero atoms chosen from oxygen and sulphur, or alternatively an amino group of structure

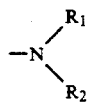

in which $R_1$ and $R_2$ may be identical or different and correspond to a hydrogen atom, a linear or branched $C_1$-$C_8$ lower alkyl radical, a $C_1$-$C_8$ lower alkyl radical interrupted by one or more hetero atoms chosen from oxygen, nitrogen or sulphur and/or substituted with one or more hydroxyl groups, $R_1$ and $R_2$ do not simultaneously denote a hydrogen atom, $R_1$ and $R_2$ also being able to form, with the nitrogen atom a heterocyclic system optionally containing nitrogen, oxygen or sulphur as an additional hetero atom;

one of the radicals $R_1$ or $R_2$ can also denote, when the other is a hydrogen atom, an aryl radical of formula (II):

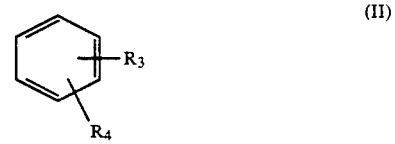

or a benzyl radical of formula (III):

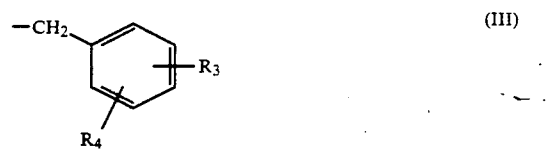

in which formulae $R_3$ and $R_4$ denote, independently of each other, a hydrogen atom, a $C_1$-$C_4$ alkyl radical, a hydroxyl group, a halogen atom such as chlorine, bromine or fluorine a carboxyl group or a trifluoromethyl group, the amino group can also originate from a sugar such as, preferably, glucosamine, and also their isomers and the pharmaceutically and cosmetically acceptable salts, such as the salts of inorganic or organic acids, for example hydrochloric, lactic, tartaric and citric acids.

The especially preferred compounds of the invention are chosen from the following compounds:

when R denotes a substituted $C_1$-$C_8$ alkoxy group, it denotes more especially a 2-hydroxyethoxy or 2-hydroxypropyloxy group or a 2,3-dihydroxypropyloxy group or its isomer, the 1,3-dihydroxy-2-propyloxy radical;

when R denotes an amino group of structure

the preferred meanings of $R_1$ and $R_2$ are as follows:

for $R_1$ and/or $R_2$ lower alkyl, methyl, ethyl, isopropyl, for $R_1$ and $R_2$ alkyl interrupted by one or more hetero atoms such as —$CH_2CH_2OCH_2CH_2OH$ for $R_1$ and/or $R_2$ $C_1$–$C_8$ alkyl substituted with one or more hydroxyl groups, the preferred meanings are as follows:
$CH_2CH_2OH$, $CH_2CHOHCH_3$, $CH_2CHOHCH_2OH$;

when $R_1$ and $R_2$ form a ring, the preferred compounds of the invention are amides of pyrrolidine, morpholine, piperazine and 4-(2'-hydroxyethyl)piperazine;

when one of $R_1$ and $R_2$ denotes H and the other an aryl radical, the latter is a para-hydroxyphenyl radical.

Among the compounds of formula I, the following may be mentioned:

2',3'-dihydroxypropyl 5,8,11-eicosatriynoate
N-(2-hydroxyethyloxyethyl)-5,8,11-eicosatriynamide
N-ethyl-5,8,11-eicosatriynamide
pyrrolidino-5,8,11-eicosatriynamide
N,N-bis(2-hydroxyethyl)-5,8,11-eicosatriynamide
N-(2-hydroxyethyl)-5,8,11-eicosatriynamide
N-(2,3-dihydroxypropyl)-5,8,11-eicosatriynamide
4'-(2-hydroxyethyl)piperazino-5,8,11-eicosatriynamide
N-(para-hydroxyphenyl)-5,8,11-eicosatriynamide.

Among the preferred compounds, the following may be mentioned:

N-(2-hydroxyethyloxyethyl)-5,8,11-eicosatriynamide
2',3'-dihydroxypropyl 5,8,11-eicosatriynoate
N-ethyl-5,8,11-eicosatriynamide
pyrrolidino-5,8,11-eicosatriynamide
4'-(2-hydroxyethyl)piperazino-5,8,11-eicosatriynamide.

These esters or amides are prepared from 5,8,11-eicosatriynoic acid, which has itself been known for a long time (see A. VAN DORP et al., Recueil 85, 1966, page 1233). The scheme A below depicts this synthesis. The synthesis of the $^{14}C$-labelled product and also the synthesis of many homologs of this acid are described in particular in the thesis by ULLMAN MYRON, 1970, Ohio State University, Ph.D., Biochemistry.

The acid, moreover, is described in U.S. patent application Ser. No. 3,033,884.

The applicants have also discovered, and this constitutes another subject of the invention, a new process for preparing 5,8,11-eicosatriynoic acid, by means of which process the esters and amides according to the invention may be produced in more advantageous yields and at more advantageous costs (Scheme B).

This process is essentially characterized in that 1-halo-2,5-tetradecadiyne (3) is synthesized in a single stage by reacting 1-decyne (1) with the 1,4-dihalo-2-butyne (2) in the presence of a strong base such as an organomagnesium compound. During this reaction, the acetylide of the decyne (1) is formed by exchange with this strong base and is then reacted with the dihalide (2) in excess and, surprisingly, the compound (3) is obtained in very good yield. The result is especially surprising when it is known that the synthesis of this halide was hitherto obtained by carrying out chain-elongation reactions using a propargyl alcohol derivative, with relatively low yields.

Reaction scheme A
(a) Synthesis of 1-bromo-2,5-tetradecadiyne

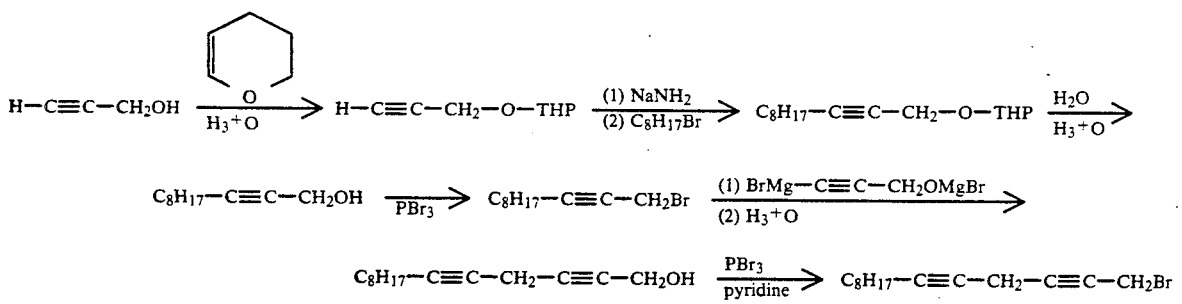

(b) Synthesis of 5-hexynoic acid

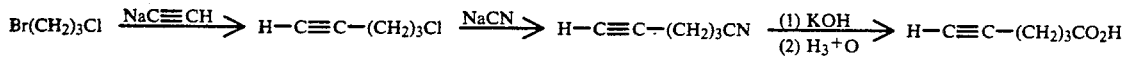

(c) Coupling reaction

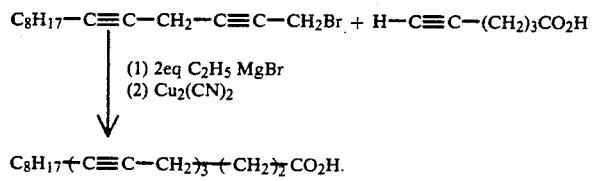

Reaction scheme B
(a) Synthesis of 1-halo-2,5-tetradecadiyne

-continued

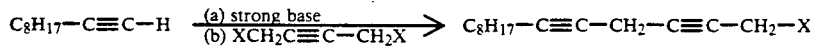

(1) (2) (3)

(b) Synthesis of 5-hexynoic acid

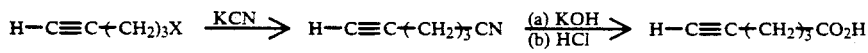

(4) (5) (6)

(c) Coupling reaction

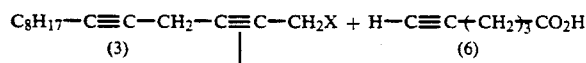

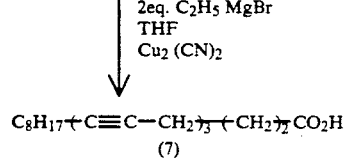

The synthesis of 5-hexynoic acid (6), which is reacted with the 1-halo-2,5-tetradecadiyne (3), is known per se and consists initially in reacting potassium cyanide with the 1-halopentyne (4). The 5-hexynenitrile (5) is then converted to the corresponding acid (6) by the action of potassium hydroxide followed by acidification of the reaction medium.

The acetylide of the acid (6) is formed by reaction with two equivalents of organomagnesium compound. The dianion is then coupled with the 1-halotetradecadiyne in an ether such as tetrahydrofuran. This reaction can optionally be performed in the presence of an aprotic solvent such as hexamethylphosphoramide (HMPA). A good yield of 5,8,11-eicosatriynoic acid (7) is then obtained.

The esters according to the invention are obtained by reactions which are known per se. They are prepared, in particular, according to a first method by reaction of phosphorus pentachloride with the acid of formula (7), followed by the reaction of the corresponding acid chloride (8) with an alcohol (9) (R'—OH), R' is a $C_1$-$C_8$ lower alkyl or a $C_4$-$C_6$ cycloalkyl group, substituted with one or more hydroxyl groups and/or interrupted by one or more hetero atoms chosen from oxygen and sulphur. This reaction corresponds to the following scheme :

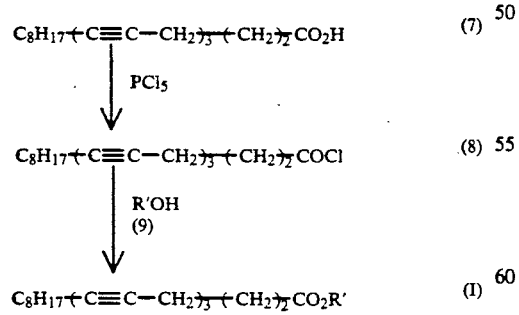

The second method uses the process described in H. NORMANT et al., Synthesis 1975, page 805, which consists in forming the potassium salt of the acid in DMF by reaction with potassium bicarbonate in the presence of a diamine (N,N,N',N'-tetramethyl-1,3-propylenediamine). The potassium carboxylate is then reacted with a halide of formula (R'—X), where R' is as defined above and X denotes a halogen such as Br or Cl:

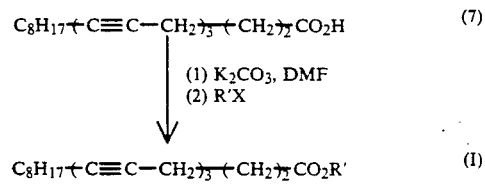

When the first method is used and the radical R' is substituted with at least two hydroxyl groups, such as, for example, the ester of glycerol, it is preferable to protect two of the three hydroxyl groups in the form of dioxolane (11), according to the following reaction scheme:

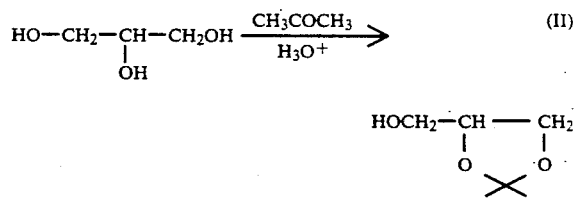
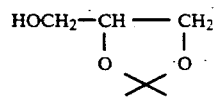

The dioxolane (11) is then reacted with the acid chloride (8). The ester (12) thereby obtained is treated under mild conditions in methanol in the presence of an acid catalyst to remove the group protecting the two alcohol groups, according to the following reaction scheme:

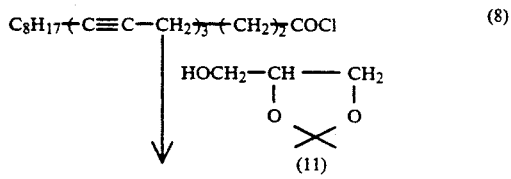
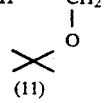

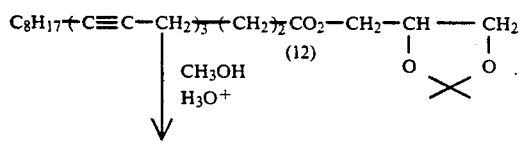

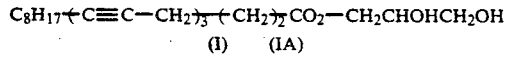

and/or

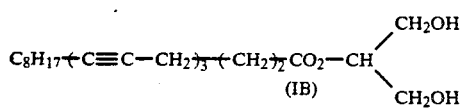

The amides according to the invention can be obtained by two methods.

The first method consists in reacting the acid chloride (8) with the amine

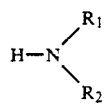

in the presence of a tertiary amine, according to the following reaction scheme:

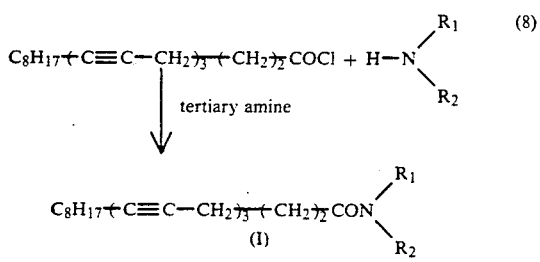

The second method employs a known process described in HEINZ A. STAAB, Liebigs Ann. Chem., 1957, 609, 75. In this process, the acid (7) is reacted in DMF, brought to 80° C., with carbonyldiimidazole (CDI) for 2 to 3 hours. An excess of amine of formula

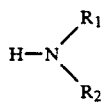

is then added at room temperature to the intermediate formed, according to the following reaction scheme:

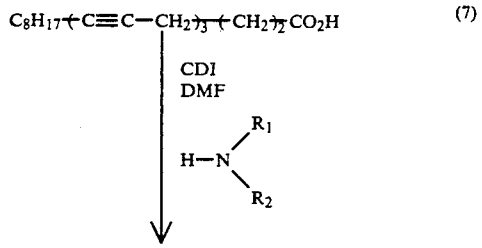

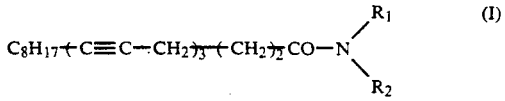

in which $R_1$ and $R_2$ have the meanings stated above.

The compounds of formula (I) according to the invention have especially notable activity in respect of the inhibition of the metabolism of arachidonic acid, particularly as regards the lipoxygenases which are at the source of the formation of the leukotrienes and the hydroxylated acids which perform an important role in the inflammatory process.

The compounds according to the invention can be administered to humans or animals by means of compositions containing, in addition, a pharmaceutically acceptable carrier or diluent. These compositions can also optionally contain other active substances which do not have an antagonistic effect on the compounds according to the invention.

The compounds according to the invention can be administered systemically or locally.

For enteral administration, the drugs can take the form of tablets, gelatin capsules, dragees, syrups, suspensions, solutions, powders, granules, emulsions and the like. For topical administration, the pharmaceutical compositions based on compounds according to the invention take the form of ointments, tinctures, creams, salves, powders, patches, impregnated pads, solutions, lotions, gels, sprays or suspensions.

These compounds for topical administration can take either anhydrous form or the form of an aqueous solution, according to the clinical indication.

The compounds according to the invention can also be administered parenterally and, in particular, intravenously, intramuscularly, intraperitoneally, subcutaneously or intradermally.

For parenteral administrations, and more especially injections, the active substance is used in a sterile vehicle such as water. The active substance is either suspended or dissolved in the vehicle.

The compounds according to the invention can also be used in cosmetics, in particular in creams and skin lotions, such as in products for use before exposure to sunlight, soothing products for use after exposure to sunlight, antiseborrhoeic products or products for treating acne.

These medicinal and cosmetic compositions according to the invention can contain inert additives or pharmcodynamically or cosmetically active additives, and in particular:

hydrating agents such as thiamorpholinone and its derivatives or urea; antiseborrhoeic agents, such as S-carboxymethylcysteine, S-benzylcysteamine and their derivatives, tioxolone; antibiotics such as erythromycin, neomycin or tetracyclins; agents which promote the regrowth of hair, such as minoxidil (2,4-diamino-6-piperidinopyrimidine 3-oxide) and its derivatives, diazoxide and phenytoin; other steroid or non-steroid antiinflammatory agents; carotenoids and in particular β-carotene; antipsoriasitic agents such as anthralin and its derivatives; and phospholipase $A_2$ inhibitors.

These compositions can also contain taste-improvement agents, preservatives, stabilizers, moisture regulators, pH regulators, osmoti pressure-modifying agents, emulsifiers, UV-A and UV-B filters, antioxidants such as α-tocopherol, butylated hydroxyanisole or butylated hydroxytoluene, local aneasthetics, buffers, and the like.

They can also be packaged in delayed-release or slow-release forms which are known per se. Finally, they can be introduced into aqueous phases of liposomes or niosomes.

The active substance according to the invention is present in the compositions in proportions of between 0.01 and 10% by weight relative to the total weight of the composition, and preferably between 0.01 and 5%.

In therapeutic application, the treatment is determined by the doctor and can vary depending on the age, weight ad response of the patient, as well as on the severity of the symptoms. The dosage is generally between 0.05 and 300 mg/kg/day, and preferably 0.5 to 100 mg/kg/day. The period of treatment is variable depending on the severity of the symptoms, and can extend for between 1 and 12 weeks in continuous or discontinuous fashion.

In cosmetic application, the compositions according to the invention are mainly used as products for use before exposure to sunlight and soothing products for use after exposure to sunlight, and for the treatment of seborrhoeic dermatitis and/or dermatitis involving acne.

The examples which follow are intended to illustrate the invention without thereby being limitative in nature.

REFERENCE EXAMPLE

Preparation of 5,8,11-eicoSatriynoic acid a) Preparation of 1-chloro-2,5-tetradecadiyne 19.35 g of magnesium (0.79 gramme-atom) and then 750 cm$^3$ of anhydrous tetrahydrofuran (THF) are placed in a 2-liter round-bottomed flask equipped with a stirrer and an argon inlet. 90.25 g of ethyl bromide (1.15 equivalent) are then introduced dropwise so as to maintain the THF refluxing. When the addition is complete, this refluxing is maintained until the magnesium has been completely converted. 100 g of 1-decyne (0.72 mol) are then added dropwise at this temperature in the course of approximately half an hour, and the mixture is maintained refluxing for a further hour and a half after the addition is complete. 5.20 g of cuprous cyanide are then introduced and boiling is maintained for a further hour. To the 1-decyne acetylide thereby formed, 250 g of 1,4-dichloro-2-butyne, or 2.8 equivalents with respect to the decyne, are added at a temperature maintained at between 40° and 50° C. Boiling is maintained for 5 hours. The solvent is removed in a rotary evaporator. The oily mass obtained is cooled and stirred in the presence of 350 cm$^3$ of water saturated with ammonium chloride, and then extracted 3 times with ether. The ether phase is washed twice with water, dried over magnesium sulphate and then concentrated at normal pressure, and the remaining ether is then removed under a pressure of $26.6 \times 10^2$ Pa. The crude 1-chloro-2,5-tetradecadiyne is distilled at a temperature of between 118° C. and 125° C. under 2.6 Pa. In the final fractions at between 125° C. and 130° C. under 4 Pa, the remainder of the expected product is distilled mixed with 1-bromo-2,5-tetradecadiyne, which forms during the reaction by exchange of chlorine with bromine.

100 g of 1-chloro-2,5-tetradecadiyne containing approximately 3 to 5% of 1-bromo-2,5-tetradecadiyne are obtained, determined by proton NMR, and this used as it is in the final coupling stage.

b) Preparation of 5-hexynoic acid

A solution of 115 g of 1-chloro-4-pentyne (1.12 mole) in 100 cm$^3$ of anhydrous dimethyl sulfoxide (DMSO) is introduced dropwise at a temperature of between 40° and 50° C. into a solution, placed under an inert atmosphere, of 60.4 g of sodium cyanide (1.23 mole) in 200 cm$^3$ of anhydrous DMSO. The reaction is exothermic and it is necessary to cool the reaction mixture to maintain the temperature below 70° C. When the addition is complete, the mixture is brought to between 60° and 70° C. for 5 hours and then left overnight at 20° C. It is then poured into 1.5 liters of water. The mixture obtained is extracted four times with 200 cm$^3$ of ether. The ether phases are combined, then washed twice with 60 cm$^3$ of water and dried over sodium sulphate. The ether is distilled off under reduced pressure. 101 g of 5-hexyne-1-nitrile are obtained. This is a yellow liquid which is used directly for the following stage. The $^1$H NMR and IR spectra correspond to the expected structure.

200 g of the above nitrile (2.15 moles) are introduced into 2.5 liters of 2N potassium hydroxide. This mixture is stirred for two hours at 90° C. and then cooled to 0° C.; 5N hydrochloricaacid is then added to the mixture until the pH≃4. The mixture is extracted four times with 300 cm$^3$ of ether. The combined ether phases are washed twice with aqueous ammonium chloride solution, then dried over magnesium sulphate and concentrated under reduced pressure.

230 g of 5-hexynoic acid are obtained. This is a liquid at room temperature which crystallizes at 0° C.. The NMR and IR spectra correspond to the expected structure.

| Elementary analysis: $C_6H_8O_2$ | | | |
|---|---|---|---|
| | C | H | O |
| Calculated | 64.27 | 7.19 | 28.54 |
| Found | 64.32 | 7.21 | 28.41 | c) Preparation of 5,8,11-eicosatriynoic acid

In 200 cm$^3$ of THF, 20.05 g of magnesium (0.835 gramme-atom) are converted as above to ethyl magnesium bromide by adding 91 g of ethyl bromide (0.835 mole). This ethyl magnesium bromide solution is added to a separately prepared solution, stirred at 0° C. under an inert atmosphere, containing 46.64 g of 5-hexynoic acid (0.417 mole) in 200 cm$^3$ of anhydrous THF.

When the addition is complete, 25 cm$^3$ of hexamethylphosphoramide are added, followed by 2.5 g of cuprous cyanide. The mixture thereby obtained is then brought for approximately one hour to a temperature of 50° C. to ensure the complete conversion of the 5-hexynoic acid to the corresponding acetylide in the form of magnesium carboxylate.

A solution containing 0.32 mole of 1-chlorotetradecadiyne in 100 cm$^3$ of THF is added dropwise to this mixture at a temperature of between 40° and 50° C.

The reaction medium is brought to refluxing of the THF for 21 hours. At this stage, a further 1.3 g of cuprous cyanide is added and refluxing is still maintained for a further 8 hours. The solvent is evaporated off. The viscous liquid obtained is acidified by adding 100 cm$^3$ of 4N sulphuric acid, followed by 100 cm$^3$ of 2N sulphuric acid. The heterogenous mixture obtained is extracted three times with 250 cm$^3$ of ether. The ether phases are combined and washed twice using 150 cm$^3$ of saturated aqueous ammonium chloride solution, decanted, dried over sodium sulphate and concentrated. The product obtained is taken up with 100 cm³ of hexane and cooled to 0° C.

The crystals are drained, washed with ice-cold hexane and dried. 48 g of 5,8,11-eicosatriynoic acid, of melting point 69°-70° C., are obtained.

The ¹H NMR and IR spectra correspond to the expected structure.

PREPARATION EXAMPLE 1

Preparation of 2,3-dihydroxypropyl 5,8,11-eicosatriynoate a) Preparation of 5,8,11-eicosatriynoic acid chloride 4.1 g of phosphorus pentachloride are added slowly to a solution, stirred at 0° C., of 4 g of 5,8,11-eicosatriynoic acid in 50 cm³ of anhydrous methylene chloride. After a quarter of an hour, the solution is brought to reflux for two hours, after which time all the acid is converted. The solvent and the phosphorus oxychloride are evaporated off under reduced pressure. The acid chloride is thereby obtained and this will be used in the crude state for the subsequent reactions.

b) Preparation of the ester of the alcohol 2,2-dimethyl-4-hydroxymethyl-1,3-dioxolane The acid chloride obtained in stage a), solubilized in 30 cm³ of anhydrous methylene chloride, is added to a mixture of 2.5 cm³ of pyridine and 5 cm³ of 2,2-dimethyl-4-hydroxymethyl-1,3-dioxolane in 50 cm³ of methylene chloride, stirred at 0° C. under an inert atmosphere. The solution obtained is then left overnight at room temperature.

The reaction medium is washed with water, and the organic phase is dried over magnesium sulphate and then deposited on a chromatography column of silica gel. The expected ester is eluted with an ethyl acetate/hexane (1:9) mixture. After concentration of the elution phases, 2.7 g of ester are isolated in the form of a viscous liquid, the ¹H NMR and IR spectra of which correspond to the expected structure.

c) Release of the protective group from the 2,3-dihydroxypropyl group

A solution of 2 g of the above protected ester is stirred at room temperature in 30 cm³ of methanol in the presence of 2.2 g of Amberlite (sulphonic H+ resin) for three days.

It is ensured at this stage, using verification by thin layer chromatography, that the 1,3-dioxolane portion is converted to the corresponding diol. The resin is then removed by filtration. The methanol is evaporated off under reduced pressure, the liquid obtained is solubilized in the minimum of methylene chloride and the solution obtained deposited on a column of silica gel.

The ester is eluted with an ethyl acetate/hexane (75:25) mixture.

After concentration of the elution phases, 1.1 g of 2,3-dihydroxypropyl 5,8,11-eicosatriynoate is obtained. The base peak (m/e:374) in mass spectrography corresponds well to the expected molar mass (M=374). The ¹H and ¹³C 250-MHz NMR spectra show that this product contains approximately 8% of its isomer, 1,3-dihydroxy-2-propyl 5,8,11-eicosatriynoate.

PREPARATION EXAMPLE 2

Preparation of N-(2-hydroxyethyloxyethyl)-5,8,11-eicosatriynamide (1st synthesis route)

A solution of 1 g of eicosatriynoic acid chloride is added slowly to a mixture, cooled to 0° C. under an inert atmosphere, of 0.36 g of Diglycolamine and 0.23 cm³ of triethylamine in 20 cm³ of methylene chloride. The conversion of the acid chloride, followed by thin layer chromatography, is very rapid. When this is complete, the reaction medium is poured into 100 cm³ of ice-cold water. The organic phase is decanted. The aqueous phase is extracted again three times with methylene chloride. The methylene chloride phases are combined, washed with water saturated with ammonium chloride, then dried over magnesium sulphate and concentrated. 0.6 g of amide is thereby isolated and this purified by passage through a column of silica gel. The amide is eluted with ethyl acetate. After evaporation of the eluent, 0.4 g of N-(2-hydroxyethyloxyethyl)-5,8,11-eicosatriynamide is obtained in the form of beige crystals, the melting point of which is 60° C.

The 250 MHz ¹³C, infrared and mass spectra correspond to the expected structure.

PREPARATION EXAMPLE 3

Preparation of N-(2-hydroxyethyloxyethyl)-5,8,11-eicosatriynamide (2nd synthesis route)

A stirred solution of 15 g of 5,8,11-eicosatriynoic acid in 150 cm³ of anhydrous dimethyl formamide is prepared under an atmosphere of argon, to which 10.5 g of carbonyldiimidazole are added at room temperature. The mixture is then brought for three hours to a temperature of between 70° and 80° C. The mixture is cooled to 0° C. and 10.5 g of Diglycolamine are then added dropwise.

The mixture is stirred for a further quarter of an hour after the addition is complete and then left overnight at room temperature and poured onto 300 g of ice. The product precipitates. It is filtered off, washed with water and dried. The 18 g of amide are then recrystallized in 150 cm³ of acetonitrile. 17 g of N-(2-hydroxyethyloxyethyl)-5,8,11-eicosatriynamide are obtained in the form of white crystals, the melting point of which is 63° C.

| Elementary analysis: $C_{24}H_{37}NO_3$ | | | | |
| --- | --- | --- | --- | --- |
| | C | H | N | O |
| Calculated | 74.37 | 9.62 | 3.61 | 12.38 |
| Found | 74.38 | 9.84 | 3.86 | 12.54 |

PREPARATION EXAMPLE 4

Preparation of N-ethyl-5,8,11-eicosatriynamide

A stirred mixture, under an atmosphere of argon, of 1 g of 5,8,11-eicosatriynoic acid and 0.7 g of carbonyldiimidazole in 10 cm³ of anhydrous DMF is brought for 3 hours to a temperature of 80° C.

A 33%-strength aqueous solution of N-ethylamine is then added at 0° C. in a single portion. After one hour, it is verified that the starting acid is completely converted to the corresponding amide. The reaction mixture is poured into 100 cm³ of ice-cold water. The precipitated product is drained, washed with water and dried. 1.1 g of solid is obtained and this is recrystallized in 10 cm$^3$ of ice-cold acetonitrile.

0.85 g of N-ethyl-5,8,11-eicosatriynamide is thereby isolated in the form of white crystals, the melting point of which is 68° C.

| | Elementary analysis: C$_{22}$H$_{33}$NO | | | |
|---|---|---|---|---|
| | C | H | N | O |
| Calculated | 80.68 | 10.15 | 4.27 | 4.88 |
| Found | 80.82 | 10.37 | 4.21 | 5.10 |

PREPARATION EXAMPLE 5

Preparation of pyrrolidino-5,8,11-eicosatriynamide 0.7 g of carbonyldiimidazole is added in a single portion to a solution, stirred under an atmosphere of argon, of 1 g of 5,8,11-eicosatriynoic acid in 10 cm$^3$ of anhydrous DMF. The solution is then brought for three hours to 80° C. 0.5 g of pyrrolidine is then introduced at 0° C. After two hours, the reaction is complete.

The reaction mixture is then poured into 100 cm$^3$ of ice-cold water followed by extraction with methylene chloride. The organic phase is washed with hydrochloric acid solution and then with water until the pH is neutral, dried over sodium sulphate and concentrated. 1.1 g of pyrrolidino-5,8,11-eicosatriynamide is obtained in the form of a yellow liquid.

The IR and 250 MHz $^1$H NMR spectra are in agreement with the expected structure.

The elementary analysis corresponds to a hemihydrate: C$_{24}$H$_{35}$NO.1/2H$_2$O.

| | C | H | N |
|---|---|---|---|
| Calculated | 79.50 | 10.00 | 3.86 |
| Found | 79.22 | 9.38 | 4.00 |

PREPARATION EXAMPLE 6

Preparation of N,N-bis(2-hydroxyethyl)-5,8,11-eicosatriynamide

The intermediate formed from 1 g of acid and 0.7 g of carbonyl diimidazole in 10 cm$^3$ of anhydrous DMF is treated with 1 g of diethanolamine.

When all the acid is converted, the dimethylformamide is evaporated off under reduced pressure. The liquid obtained is solubilized in methylene chloride and washed in acid medium, and the organic phase is dried over sodium sulphate and then stirred in the presence of 15 g of silica gel. This gel, to which the amide is bound, is filtered off. The amide is then released by extracting the silica with ethyl acetate.

After evaporation of the solvent, 0.8 g of N,N-bis(2-hydroxyethyl)-5,8,11-eicosatriynamide is obtained. At room temperature, it is a yellow liquid, the IR and 250 MHz $^1$H NMR spectra of which are in agreement with the expected structure.

PREPARATION EXAMPLE 7

Preparation of N-(2-hydroxyethyl)-5,8,11-eicosatriynamide

A solution of 8 g of 5,8,11-eicosatriynoic acid and 5.62 g of carbonyldiimidazole in 40 cm$^3$ of anhydrous DMF is brought to 80° C. for 3 hours under an inert atmosphere. 3.25 g of ethanolamine are then added at 0° C. After 2 hours, it is verified by thin layer chromatography that the starting acid is completely converted.

The reaction mixture is then concentrated by evaporation under vacuum, and then dissolved in 100 cm$^3$ of methylene chloride. The solution is washed with water and dried over sodium sulphate, and the methylene chloride removed by evaporation under vacuum. 9.1 g of solid are obtained. After recrystallization of the latter, 8 g of N-(2-hydroxyethyl)-5,8,11-eicosatriynamide are isolated in the form of white crystals, the melting point of which is 87° C.

The IR and 250 MHz $^1$H NMR spectra correspond to the expected structure.

| | Analysis: C$_{22}$H$_{33}$NO$_2$ | | | |
|---|---|---|---|---|
| | C | H | N | O |
| Calculated | 76.92 | 9.68 | 4.01 | 9.31 |
| Found | 77.04 | 9.73 | 4.11 | 9.50 |

PREPARATION EXAMPLE 8

Preparation of N-(2,3-dihydroxypropyl)-5,8,11-eicosatriynamide

In the same manner as in the above example, 8 g of 5,8,11-eicosatriynoic acid in 40 cm$^3$ of anhydrous DMF are treated initially with 5.62 g of carbonyldiimidazole. 4.1 cm$^3$ of 2,3-dihydroxypropylamine are then added at 0° C. At the end of the reaction, the reaction mixture is poured into ice-cold water. The precipitated product is drained and dissolved in 300 cm$^3$ of methylene chloride. The solution is dried over sodium sulphate and then concentrated under reduced pressure. The solid obtained is directly recrystallized in acetonitrile. 9 g of N-(2,3-dihydroxypropyl)-5,8,11-eicosatriynamide are thereby obtained in the form of very pale beige crystals of melting point 87° C.

The IR and 250 MHz $^1$H NMR spectra are in agreement with the expected structure.

| | Elementary analysis: C$_{23}$H$_{35}$NO$_3$ | | | |
|---|---|---|---|---|
| | C | H | N | O |
| Calculated | 73.95 | 9.44 | 3.75 | 12.85 |
| Found | 73.85 | 9.50 | 3.93 | 12.65 |

PREPARATION EXAMPLE 9

Preparation of 4'-(2-hydroxyethyl)piperazino-5,8,11-eicosatriynamide

A mixture of 1 g of 5,8,11-eicosatriynoic acid and 0.7 g of carbonyldiimidazole (CDI) in 5 cm$^3$ of anhydrous DMF is stirred under an inert atmosphere for 3 hours at a temperature between 70° and 80° C. The solution is then cooled to 0° C. and a solution of 0.8 g of 1-(2-hydroxyethyl)piperazine in 5 cm$^3$ of DMF is then added. Stirring is maintained for 2 hours and the reaction medium is left overnight. The solvent is evaporated off under reduced pressure. The liquid obtained is taken up with methylene chloride and the solution is washed several times with water, dried over sodium sulphate and concentrated under reduced pressure. 0.8 g of 4'-(2-hydroxyethyl)piperazino-5,8,11-eicosatriynamide is obtained in the form of a yellow liquid.

The IR and 250 MHz $^1$H spectra correspond to the expected structure. The elementary analysis corresponds to a partially hydrated product.

| Elementary analysis: $C_{26}H_{40}N_2O_2 \cdot \frac{1}{2}H_2O$ | | | | |
|---|---|---|---|---|
| | C | H | N | O |
| Calculated | 74.86 | 9.78 | 6.71 | 8.63 |
| Found | 74.42 | 10.42 | 6.72 | 8.49 |

PREPARATION EXAMPLE 10

Preparation of
N-(para-hydroxyphenyl)-5,8,11-eicosatriynamide

In the same manner as in the above example, the intermediate formed from 1 g of 5,8,11-eicosatriynoic acid and 0.7 g of CDI is treated with 0.727 g of para-hydroxyaniline. The medium is then stirred for 24 hours at room temperature. Water is then added gradually to the mixture until all the product formed precipitates. It is drained and dried and then recrystallized in isopropyl ether. 0.85 g of N-(para-hydroxyphenyl)-5,8,11-eicosatriynamide is obtained in the form of beige-white crystals of melting point 121° C.

The infrared and 250 MHz 1H NMR spectra are in agreement with the expected structure.

| Elementary analysis: $C_{26}H_{33}NO_2$ | | | | |
|---|---|---|---|---|
| | C | H | N | O |
| Calculated | 79.75 | 8.49 | 3.57 | 8.17 |
| Found | 79.68 | 8.51 | 3.70 | 8.35 |

The examples which follow are intended to illustrate compositions according to the invention.

EXAMPLE 1

The following composition is prepared:

| | |
|---|---|
| 2,3-Dihydroxypropyl 5,8,11-eicosatriynoate | 0.50 g |
| 1-Propanol | 50.00 g |
| Propylene glycol | 10.00 g |
| Hydroxypropylcellulose | 2.00 g |
| Water qs | 100 g |

This composition takes the form of a gel which can be applied topically. Good results are also obtained by replacing 2,3-dihydroxypropyl 5,8,11-eicosatriynoate in the composition by N-(2-hydroxyethyloxyethyl)-5,8,11-eicosatriynamide.

EXAMPLE 2

The following composition is prepared:

| | |
|---|---|
| N-(2-Hydroxyethyl)-5,8,11-eicosatriynamide | 5.0 g |
| Micronized polyethylene | 10.00 g |
| Isopropyl myristate qs | 100 g |

This composition takes the form of a hydrophobic ointment intended for topical application. Good results are also obtained by replacing N-(2-hydroxyethyl)-5,8,11-eicosatriynamide in this ointment by N-(2,3-dihydroxypropyl)-5,8,11-eicosatriynamide or by N-(2-hydroxyethyloxyethyl)-5,8,11 eicosatriynamide.

EXAMPLE 3

The following composition is prepared:

| | |
|---|---|
| N-Ethyl-5,8,11-eicosatriynamide | 1.00 g |

| -continued | |
|---|---|
| Capric, caprylic and stearic acid triglycerides | 40.00 g |
| Capric and caprylic acid triglycerides | 30.00 g |
| Vaseline | 20.00 g |
| Liquid paraffin qs | 100 g |

This composition takes the form of a hydrophobic ointment intended for topical application.

It is possible to replace N-ethyl-5,8,11-eicosatriynamide in this ointment by pyrrolidino-5,8,11-eicosatriynamide.

EXAMPLE 4

The following composition is prepared:

| | |
|---|---|
| 4'-(2-Hydroxyethyl)piperazino-5,8,11-eicosatriynamide | 0.50 g |
| Cetyl alcohol | 6.40 g |
| Cetyl alcohol oxyethylenated with 20 moles of ethylene oxide | 2.10 g |
| Glycerol monostearate | 2.00 g |
| Capric and caprylic acid triglycerides | 15.00 g |
| Propylene glycol | 10.00 g |
| Water qs | 100 g |

This composition takes the form of a cream intended for topical application.

EXAMPLE 5

The following lotion is prepared:

| | |
|---|---|
| 2,3-Dihydroxypropyl 5,8,11-eicosatriynoate | 0.10 g |
| Ethanol | 50.00 g |
| Propylene glycol qs | 100 g |

This lotion is used for topical application.

The compositions of Examples 1 to 5 above are all manufactured and stored in an inert atmosphere and shielded from the light.

EXAMPLE 6

The following composition is prepared:

| | |
|---|---|
| 2,3-Dihydroxypropyl 5,8,11-eicosatriynoate | 0.01 g |
| Absolute ethanol | 1.00 ml |
| Flavouring qs, preservative qs, glycerole qs | 5.00 ml | which is introduced into a 5-ml brown glass ampoule and intended for use orally in the form of a solution to be taken by mouth.

EXAMPLE 7

A 350-mg gelatin capsule is prepared containing a powder which has the following composition:

| | |
|---|---|
| N-(2-Hydroxyethyloxyethyl)-5,8,11-eicosatriynamide | 0.025 g |
| Microcrystalline cellulose | 0.020 g |
| Maize starch | 0.100 g |
| Colloidal silica | 0.020 g |
| Magnesium stearate | 0.185 g |

What is claimed is:

1. A compound having the formula $$C_8H_{17}(-C\equiv C-CH_2-)_3CH_2CH_2COR \qquad (I)$$

wherein

R is a $C_1$-$C_8$ lower alkoxy or $C_4$-$C_6$ cycloalkoxy group, said alkoxy or said cycloalkoxy group being substituted with one or more hydroxyl groups and-/or interrupted by one or more hetero atoms chosen from oxygen and sulfur.

2. The compound of claim 1, wherein COR is an ester group of a glycol, glycerol, polyethylene glycol or a sugar.

3. The compound of claim 1 wherein R is —O—CH$_2$—CH$_2$—OH, —O—CH$_2$—CH—OH—CH$_3$, —O—CH$_2$—CHOH—CH$_2$—OH or

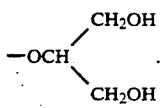

4. The compound of claim 1 which is 2,3-dihydroxypropyl-5,8,11-eicosatriynoate.

5. A pharmaceutical composition for oral or local administration comprising a pharmaceutically acceptable carrier or diluent and a therapeutically effective amount of at least one active compound of claim 1.

6. A pharmaceutical composition for topical administration in the form of a cream, tincture, ointment, salve, powder, patch, impregnated pad, solution, gel, lotion, spray or suspension comprising a therapeutically effective amount of at least one compound of claim 1.

7. A pharmaceutical composition for parenteral administration intravenously, intramuscularly, subcutaneously or intradermally, comprising a therapeutically effective amount of at least one active compound of claim 1 in a pharmaceutically acceptable diluent.

8. A pharmaceutical composition for enteral administration in the form of a tablet, gelatin capsule, dragee, syrup, suspension, solution, powder, granule or emulsion comprising a therapeutically effective amount of at least one active compound of claim 1.

9. The pharmaceutical composition of claim 5 wherein said active compound is present in an amount ranging from 0.1 to 10 percent by weight based on the total weight of said composition.

10. The pharmaceutical composition of claim 5 wherein said active compound is present in an amount ranging from 0.1 to 5 percent by weight based on the total weight of said composition.

11. A cosmetic composition comprising in a cosmetically acceptable carrier at least one active compound of claim 1 in an amount ranging from 0.01 to 10 percent by weight based on the total weight of said composition.

12. The cosmetic composition of claim 11 wherein said active compound is present in an amount ranging from 0.1 to 5 percent by weight.

* * * * *